US008771640B2

(12) United States Patent
Selwyn

(10) Patent No.: US 8,771,640 B2
(45) Date of Patent: Jul. 8, 2014

(54) SYSTEM AND METHOD FOR USING GLASS MICROSPHERES CONTAINING A POSITRON-EMITTING ISOTOPE TO IMAGE BLOOD FLOW AND DISTRIBUTE A RADIOMEDICAL TREATMENT SPECIES

(76) Inventor: Reed Selwyn, Clarksburg, MD (US)

( * ) Notice: Subject to any disclaimer, the term of this patent is extended or adjusted under 35 U.S.C. 154(b) by 1331 days.

(21) Appl. No.: 12/015,582

(22) Filed: Jan. 17, 2008

(65) Prior Publication Data

US 2009/0016960 A1 Jan. 15, 2009

Related U.S. Application Data

(60) Provisional application No. 60/948,799, filed on Jul. 10, 2007.

(51) Int. Cl.
*A61K 51/00* (2006.01)
*A61M 36/14* (2006.01)

(52) U.S. Cl.
USPC .......................................... 424/1.11; 424/9.1

(58) Field of Classification Search
None
See application file for complete search history.

(56) References Cited

U.S. PATENT DOCUMENTS

| | | | | |
|---|---|---|---|---|
| 4,789,501 | A * | 12/1988 | Day et al. | 424/1.29 |
| 5,011,677 | A * | 4/1991 | Day et al. | 424/1.61 |
| 5,302,369 | A | 4/1994 | Day et al. | |
| 6,010,445 | A * | 1/2000 | Armini et al. | 600/3 |
| 6,537,518 | B1 * | 3/2003 | Gray | 424/1.29 |
| 2003/0059368 | A1 * | 3/2003 | Groman et al. | 424/1.11 |
| 2004/0131543 | A1 * | 7/2004 | Wong et al. | 424/1.11 |
| 2004/0197264 | A1 | 10/2004 | Schwarz et al. | |
| 2004/0258614 | A1 | 12/2004 | Line et al. | |
| 2006/0067883 | A1 | 3/2006 | Krom et al. | |
| 2008/0038190 | A1 * | 2/2008 | Simpson et al. | 424/1.13 |

FOREIGN PATENT DOCUMENTS

| | | |
|---|---|---|
| EP | 1162626 | 12/2001 |

OTHER PUBLICATIONS

McCarthy et al. Nucl. Med. Biol. 1997, 24, 35-43.*
Sun et al. Biomacromolecules. 2005; 6(5): 2541-2554.*
Avila-Rodriguez et al. Positron-emitting resin microspheres as surrogates of 90Y SIR-spheres: a radiolabeling and stability study. Nuclear Medicine and Biology, 34, 2007, 585-590.

* cited by examiner

*Primary Examiner* — Michael G Hartley
*Assistant Examiner* — Sean R Donohue
(74) *Attorney, Agent, or Firm* — C. John Brannon; Brannon Sowers & Cracraft PC

(57) ABSTRACT

A method for imaging the blood flow in a patient receiving radiomedical treatment, including forming a first and a second plurality of generally spherical biologically stable members, with each respective member of the first plurality includes a first non-radioactive isotope distributed substantially uniformly therein that, upon being subjected to an effective amount of neutron irradiation, emits a therapeutic intensity and amount of beta or gamma radiation and wherein each respective member of the second plurality includes a second non-radioactive isotope distributed substantially uniformly therethrough that, upon being subjected to an effective amount of neutron irradiation, emits a detectable intensity and amount of positron radiation. The first and second members are subjected to an effective amount of neutron radiation and the irradiated first and second pluralities of irradiated first and second members are introduced into a patient's circulatory system upstream of a desired treatment site. The second plurality of irradiated members is imaged via positron emission tomography. The second isotope, once activated by neutron irradiation, has a maximum half-life of about four days.

13 Claims, 1 Drawing Sheet

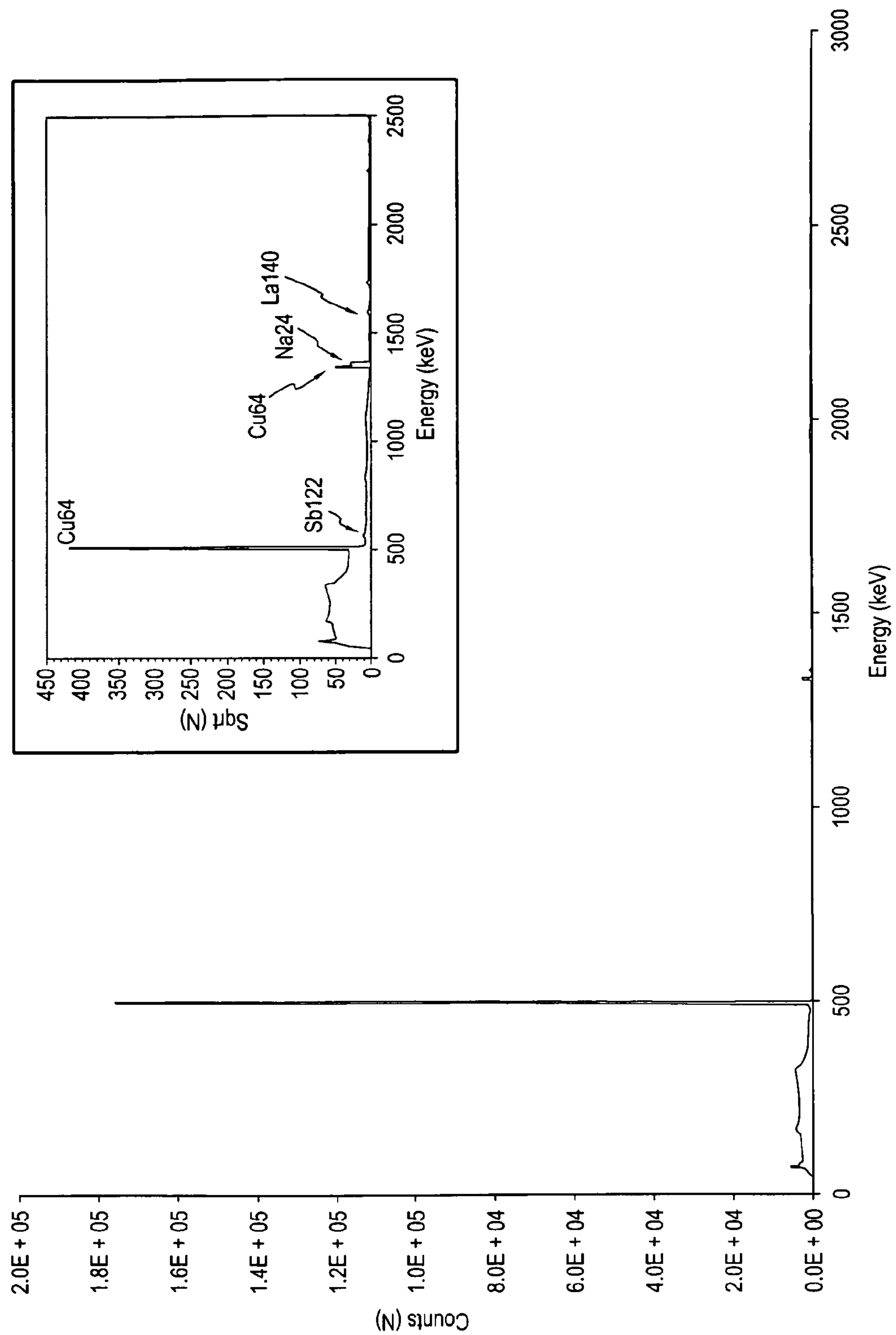
Counts (N)
2.0E + 05
1.8E + 05
1.6E + 05
1.4E + 05
1.2E + 05
1.0E + 05
8.0E + 04
6.0E + 04
4.0E + 04
2.0E + 04
0.0E + 00
0
500
1000
1500
2000
2500
3000
Energy (keV)
Sqrt (N)
450
400
350
300
250
200
150
100
50
0
Cu64
Sb122
Cu64
Na24
La140
Energy (keV)

SYSTEM AND METHOD FOR USING GLASS MICROSPHERES CONTAINING A POSITRON-EMITTING ISOTOPE TO IMAGE BLOOD FLOW AND DISTRIBUTE A RADIOMEDICAL TREATMENT SPECIES

CROSS-REFERENCE TO RELATED APPLICATIONS

This patent application claims priority to co-pending U.S. Provisional Patent Application Ser. No. 60/948,799, filed Jul. 10, 2007.

TECHNICAL FIELD

The present invention relates generally to glass science and, more particularly, to radioactive glass microspheres useful for radiomedical treatment and mapping.

BACKGROUND

One common approach to the treatment of patients with certain kinds of cancer, such as liver cancer, is to introduce radioactive particles into the patient's circulatory system, wherein the radioactive particles are targeted to the site of the cancer. Specifically, a measured amount of radioactive isotopes are injected into the patient such that they accumulate at the site of the cancer. The lodged particles thus generate a predetermined field of radiation proximate to the location of a cancerous tumor. The particular radioactive isotope is typically selected according to the type of radiation emitted and its half-life, such that the radiation has enough range to be destructive to the adjacent tumor but does only minimal damage to more remote tissue and also such that the emission of radiation lasts for only a short, predetermined duration.

One early radioisotope was yttrium, usually in oxide form, since radioactive yttrium emits nearly 100 percent beta radiation. The yttrium oxide was initially suspended in a viscous liquid medium and introduced via injection. However, yttria's high density (5.01 gm/cm$^3$) and its inherently irregular particle shape resulted in: a) difficulties in maintaining a homogeneous suspension (and thus treat the patient with a known and controlled radiation dosage); b) difficulties in concentrating all of the radioisotope at the tumor site (as the heavy yttrium oxide particles tend to drop out of suspension too soon and adhere to the interior of blood vessels; and c) the sharp corners and edges of yttrium oxide particles irritate surrounding tissue in localized areas, as well as interfere with the uniform distribution of the radioactive particles in the tumor to be treated.

These problems were addressed by including the treatment radioisotopes in microspheres, such as those made of resin or crystalline ceramic cores with radioactive materials coated thereonto. These microspheres tend to be relatively light (with densities lower than that of yttrium oxide particles alone). However, whenever a microsphere comprises a core material having an external surface coating which contains the radioactive isotope there is a risk that the radioactive coating may separate from the underlying microsphere core. Any mechanical breakage of the coating can release unwanted radioactivity to other parts of the human body which is highly undesirable. Further disadvantages are presented by the special handling and precautions that are necessary to coat a radioactive isotope onto a crystalline ceramic core, or to label ion exchange resin.

In still another application, microspheres have been prepared comprising a ceramic material and having a radioactive isotope incorporated into the ceramic material. While the inadvertent release of radioactive isotopes from a radioactive coating into other parts of the human body is reduced or eliminated by incorporating the radioisotopes into ceramic spheres, the latter product form is nevertheless not without its disadvantages. Processing of these ceramic microspheres is dangerous because potentially volatile radioactivity must be added to ceramic melts and the microspheres must be produced and sized while radioactive. Such processing steps increase the likelihood of accidental exposure of personnel and risk radioactive contamination of facilities.

Some of these drawbacks have been overcome by incorporating stable $^{89}$Y ion oxide form into glass microspheres and subsequently exposing them to neutron radiation to activate the $^{89}$Y to $^{90}$Y. The microspheres are then injected into the patient, where they become permanently lodged. Over time, the radioactivity of the microspheres decreases as the $^{90}$Y decays. The primary drawback of these glass microspheres is that the $^{90}$Y almost exclusively emits beta radiation which, while very desirable for tumor treatment, has a very short effective range and is thus difficult, if not impossible, to detect outside the body. Thus, it is difficult to track and accurately assess where the microspheres have ultimately lodged.

Thus, there remains a need for a radiomedical cancer treatment that is useful in the treatment of cancer or tumor bearing tissue, but which will not release a radioactive coating or isotope into remote parts of the body of the patient after administration, will not require any technicians to handle any radioactive materials during the formation and spheroidization of the microsphere, which have a density which will permit the microspheres to be suspended in a fluid suitable for injection into a human, and which may be readily traced to assure accurate delivery of the radiation treatment to the desired tumor site. The present invention addresses this need.

SUMMARY OF THE INVENTION

The present invention relates to biologically stable biologically compatible microspheres including a non-radioactive isotope that can be transmuted via neutron irradiation into an imaging isotope that emits positrons detectible by positron emission tomography and a method for using the same to image blood flow and the deposition of microspheres in a patient. One object of the present invention is to provide an improved method imaging the deposition of radioactive microspheres in a patient. Related objects and advantages of the present invention will be apparent from the following description.

BRIEF DESCRIPTION OF THE DRAWINGS

FIG. 1 is a graphical illustration of a plot of detected counts of positron radiation vs. energy (keV) for glass microspheres containing $^{64}$Cu obtained 48 hours post neutron irradiation.

DESCRIPTION OF THE PREFERRED EMBODIMENTS

For the purposes of promoting an understanding of the principles of the invention and presenting its currently understood best mode of operation, reference will now be made to the embodiments illustrated in the drawings and specific language will be used to describe the same. It will nevertheless be understood that no limitation of the scope of the invention is thereby intended, with such alterations and further modifications in the illustrated device and such further applications of the principles of the invention as illustrated therein being contemplated as would normally occur to one skilled in the art to which the invention relates.

It is well known in radiomedicine that certain types of cancerous tumors may be treated by the localized introduction of short-lived radioisotopes at the tumor site. One effective method of delivering such a radiation treatment is by irradiating microspheres made of glass, resin, or a like biologically stable material that does not become substantially radioactive when exposed to neutron radiation that further include a significant amount of a predetermined radiotherapy treatment element that, upon neutron irradiation, emits gamma or beta radiation at therapeutic levels and intensities (such as activated yttrium or $^{90}Y$) dissolved or otherwise contained therein. The $^{90}Y$ or like radiotherapeutic element is typically introduced in the form of a non-radioactive stable oxide and dissolved in the glass precursor, which is formed into microspheres and subsequently activated through neutron irradiation shortly before introduction into the patient's circulatory system. Typically, the predetermined radiotherapy treatment element has a short half-life, so that the radiation treatment is relatively short in duration; more typically, the predetermined element is selected such that upon neutron irradiation, it emits relatively high energy beta particles and/or gamma rays. For example, $^{90}Y$ has a half-life of about 64 hours and emits beta particles with a mean energy of about 930 keV as well as energetic bremsstrahlung gamma rays. This technique enjoys the advantage of using microspheres prepared from stable, non-radioactive materials; the non-radioactive microspheres may be safely stored for an indefinite period and may be neutron irradiated at will to activate the predetermined radiotherapy treatment element shortly before introduction into a patient's body.

The microspheres may be formed from any convenient glass composition that is biologically compatible. Typically, the glass composition is a good solvent for small amounts of the predetermined radiotherapy treatment element (especially in oxide form) and has sufficient chemical durability such that once microspheres formed from the glass are introduced into the patient's body and lodge at the target tumor site, no significant amount of a radioactive isotope is leeched from the microspheres into the patient's body or circulated to other parts of the patient's system. Typically, the glass composition is selected such that it does not include any elements that, once irradiated, may emit any significant amount of undesired radiation.

Some typical glass compositions for radiomedicine microspheres include aluminosilicate glasses and lead silicate glasses, both of which are typically good solvents for small amounts of nearly all oxides and permit great versatility regarding control of the dose and profile of the radiation emitted thereby after irradiation. Many aluminosilicate and lead silicate glasses also have sufficient chemical durability to prevent the loss of a significant amount of the radioactive isotope into the patient's system after the microsphere is administered, yet do not need to contain any elements that may cause the microsphere to emit a significant amount of undesired radiation. Various aluminosilicate glasses and lead silicate glasses may thus be used with predetermined amounts of Y-89 dissolved therein, such as in the form of yttrium oxide-aluminosilicate (YAS) glass compositions. The density of these glasses is typically within the range of between about 2.2 and about 2.7 grams/cc, but may be as low as 2.2 grams/cc or even lower.

The microspheres are typically produced in the form of essentially void-free glass microspheres, microshells (i.e., microspheres having a hollow core), foamed glass microspheres (i.e., microsphere having a plurality of hollow cells), but may be other convenient glass or resin compositions or the like. Microshells and foamed glass microspheres represent treatment options wherein the microspheres are substantially lighter and less dense.

Microspheres for radiomedicine are generally spherical or at least substantially free of sharp edges or points, as such would increase the likelihood that the microsphere might lodge in a location other than the target tumor (more specifically, in the network of capillaries surrounding the tumor) and/or that the sharp edges might damage healthy tissue. In this context, ellipsoidal and other similarly shaped particles that do not have sharp edges or points would be considered to be substantially spherical in shape.

Radiomedicine microspheres, such as those containing radioactive $^{90}Y$, emit a therapeutic intensity and amount of short-range beta radiation that can penetrate tissue to a depth of up to about several millimeters. $^{90}Y$ is a commonly used radiotherapeutic isotope. $^{90}Y$ is a high-energy beta-emitting isotope with no primary gamma; the maximum energy of the $^{90}Y$ beta particle is 2.28 MeV with a mean energy of about 0.93 MeV. $^{90}Y$ has a half-life ($t_{1/2}$) of about 64 hours, with 94% of its radiation delivered in approximately 11 days. Typically, concentration of radioisotope in the microspheres and the amount of microspheres introduced into a patient is controlled such that they will not emit an excess amount of unwanted beta or gamma radiation that could damage healthy tissue surrounding the target tumor. Thus, the glass composition is typically engineered so that the therapeutic radioisotopes are the only constituent isotopes which emit a significant amount of beta radiation and or gamma radiation, and that the radioisotopes have a sufficiently short half-life that the beta and gamma emissions are extinguished after a relatively short period of time, typically on the order of a several hours to a few weeks. Elements such as yttrium and phosphorus which form radioisotopes having a half-life greater than about two days and less than about 30 days are typically chosen as the constituent elements which are induced to emit therapeutic radiation.

The radiomedicine microspheres discussed above are thus designed to emit high energy beta particles and/or gamma rays that have a relatively short penetration depth in tissue. While this is desired insofar as it optimizes tumor treatment while minimizing collateral tissue damage, it does pose a detection issue. Beta radiation does not lend itself to the more accurate imaging techniques, such as single-photon emission computed tomography (SPECT) or positron emission tomography (PET). Thus, it is advantageous to introduce a second set of microspheres characterized by emissions compatible with SPECT or PET techniques (referred to herein as 'imaging microspheres'), either prior to or concurrent with the radiomedicine or treatment microspheres discussed above, that facilitate PET or SPECT imaging of the blood flow patterns in the patient and also aid in imaging of where the microspheres deposit to ensure deposition around the tumor site.

As with the treatment microspheres, the composition of the imaging microspheres is selected such that, upon neutron irradiation, the imaging microspheres emit a sufficient amount of positron emissions to facilitate PET imaging. In other words, the composition of the imaging microspheres is typically chosen so that their radiation may be tailored to deliver a radiation profile that is well suited for a particular imaging technique. For instance, when desired for use with PET imaging, the imaging microspheres will typically include a short-lived positron emitter, such as Cu-64 (half-life of 12.7 hours) or F-18 (half-life of 110 minutes) or the like. Cu-64 and F-18 are particularly attractive positron emitters, as they have short half-lives and emit low energy positrons that annihilate with electrons to produce two 511 keV gammas, which facilitates PET imaging. If longer-lived positron emitters are desired, Zr-89 (half-life of 78.4 hours) or I-124 (half-life of 4.18 days) or the like may be selected.

It should be noted that $^{18}F$ is an isotope that cannot be produced via neutron irradiation, but instead is produced in a cyclotron. $^{18}F$ is produced separately and then added to the microspheres, typically as a coating on resin microspheres. Thus, $^{18}F$ is already radioactive when introduced to the microspheres and presents an additional materials handling hazard as well as a transport and storage challenge (especially since it must be transported, applied to the microspheres, introduced into a patient and imaged while enough $^{18}F$ remains to achieve PET imaging.) On the other hand, $^{64}Cu$ may be produced by activating $^{63}Cu$ via neutron irradiation, such that a stable copper source, such as copper oxide or the like, may be incorporated into glass or resin microspheres, safely stored, and activated at will prior to introduction into the patient.

The composition of the imaging microspheres is typically chosen such that the density of the imaging microspheres is the same as, or close to, the density of the treatment microspheres, so that the movement and distribution of the imaging microspheres will be similar to that of the treatment microspheres. In other instances, it may be desirable to use microspheres incorporating both treatment radioisotopes and imaging radioisotopes, such as a positron emitter (like Cu-64) along with a beta and gamma emitter (like Y-86) or a high-energy beta emitter (like Y-90), such that the therapeutic treatment microspheres may themselves be directly imaged and tracked. In one such embodiment, a beta emitter and/or a low energy gamma emitting nuclide is incorporated along with a positron emitter into the microspheres. In a specific example of this embodiment, Y-89 and Cu-63 are incorporated into the microspheres. After neutron irradiation, the Cu-64 emits significant positron radiation (which subsequently yields 511 keV gamma pairs from positron annihilation events) and Y-90 emits nearly pure beta radiation.

Likewise, the compositions of the imaging microspheres are typically chosen so that the positron emitting element is the only constituent having a relatively large cross-section for neutrons. For example, boron is a common glass-forming element, but since it also has a relatively large cross-section for neutrons, the glass compositions typically selected for the imaging microspheres typically do not include boron. More typically, except for the imaging (and optional treatment) isotopes, the constituent elements of the imaging microspheres do not contain a significant amount of any elements that have a cross-section for neutrons greater than about 200 barns.

The intensity of the imaging radiation, like that of the treatment radiation, provided by the microspheres may be varied by controlling the number of microspheres administered as well as by controlling the amount of radiation emitting isotopes contained in the microspheres. The amount of radiation emitting isotopes contained in the microspheres is likewise governed by both the amount of the stable element that will be converted to a radioelement by irradiation and by the amount of irradiation, which is in turn a function of how much of the stable element may be incorporated into a glass composition. For example, aluminosilicate glass compositions may typically incorporate up to about 30 weight percent copper oxide. More typically, substantially boria-free aluminosilicate glasses may typically incorporate between about 0.1 and about 30 weight percent copper oxide. The amount of copper oxide that may be incorporated into an aluminosilicate glass is somewhat reduced in yttria is also incorporated thereinto; with yttria in the glass, the maximum copper oxide level is about 25 weight percent.

Typically, the imaging microspheres are irradiated for a short period of time with an intense thermal neutron flux, such as that generated by a nuclear fission reactor instead of being irradiated for a significantly longer period of time with a lesser neutron flux. This technique of a short, intense irradiation of the microsphere is especially common where one or more of the constituent elements of the imaging microsphere has an undesired characteristic radiation emission and/or a half-life that is significantly greater than that of the imaging and/or treatment elements incorporated.

The imaging microspheres are typically sized and shaped to match or substantially approximate the size and shape of the treatment microspheres. Typical treatment microspheres are sized between about 5 and about 75 micrometers, with a more typical size range being between about 10 and about 50 micrometers. In the case of liver cancer treatment, the microspheres are typically sized between about 20 and about 30 micrometers, small enough to be conveniently delivered to the liver through the hepatic artery but too large to pass through the capillary bed of the liver.

The treatment and imaging microspheres are typically introduced into the patient's body via catheter, injection or the like and become lodged in the cancerous or tumor bearing tissue. The treatment and imaging microspheres are typically suspended in a liquid medium of sufficient density and viscosity such that the microspheres remain dispersed in the suspension during the administration procedure.

The imaging microspheres are produced similarly to the treatment microspheres. While the microspheres may be made from any convenient and stable biocompatible material, such as a polymer composition, such microspheres are typically made of glass. The glass may have any convenient composition having the desired concentration of imaging elements, may be made by any convenient process, and may be spheroidized by any convenient technique to produce a plurality of glass imaging microspheres of a desired shape and size. Once prepared, the glass imaging microspheres may be irradiated and subsequently administered to a patient.

In order for imaging to be successful, the imaging microspheres should emit sufficient positron radiation as required by the sensitivity of the imaging equipment used. For example, some PET units have a sensitivity of about 5100 Bq/cc. If imaging microspheres are being used to image a target organ portion having a volume of about 1000 cubic centimeters (such as the liver), then, using the values from Table 1,

TABLE 1

| Isotopes | Half-life | Mean $\beta^+$ (keV) | Intensity (%) | MeV/Bq-s |
|---|---|---|---|---|
| $^{18}F$ | 110 m | 250 | 96.7 | 0.248 |
| $^{64}Cu$ | 12.7 h | 278 | 17.4 | 0.275 |
| $^{86}Y$ | 14.7 h | 660 | 31.9 | 0.658 |
| $^{89}Zr$ | 78.4 h | 396 | 22.7 | 0.392 |
| $^{124}I$ | 4.18 d | 820 | 22.8 | 0.820 |

at least about 5.35 MBq of F, 22.8 MBq of Zr, or 29.7 MBq of Cu would be required to image a homogeneous distribution of imaging microspheres within the 1000 cc liver. If the microspheres are assumed to be confined to a much smaller volume, such as the capillary network surrounding a tumor, substantially less activity (i.e., fewer of the same microspheres) would be required for imaging.

The following examples illustrate the invention.

Example 1

An imaging microsphere glass composition was prepared by dispersing natural copper in an aluminosilicate glass matrix. Natural copper is about 69 percent Cu-63 and about 31 percent Cu-65. Upon neutron irradiation, the Cu-63 is activated to Cu-64 and the Cu-65 is activated to Cu-66. For imaging purposes, the activation of Cu-66 is irrelevant, since Cu-66 has a half-life if about 5.1 minutes and decays to negligible amounts within a few hours of the irradiation procedure. Cu-64 is a positron emitter and lends itself to PET imaging, having a low mean positron energy (resulting in less blurring) and a 'clean' energy spectrum (minimal non-PET gamma emissions). Moreover, Cu-64 emits a low energy beta particle (end-point energy of about 578 keV) about 39 percent of the time, which could contribute to the cancer treatment of the patient.

A test glass batch was prepared. The glass composition included copper dispersed in a glass formed from silica, alumina and boria and characterized by a density of about 2.6 grams per cubic centimeter. Glass particles were sized to between 38 and 55 μm, and 100 mg samples were irradiated with neutrons for 1 hour. Neutron fluxes and Cu-63 capture cross-sections are given as Table 2. Three hours after the samples were removed from the reactor, the average activity was measured to 2 percent precision to be 207.9 MBq or 5.62 mCi.

TABLE 2

| | Flux (neatrons/cm$^2$-sec) | $^{63}$Cu $\sigma_c$ (barns) |
|---|---|---|
| Thermal | $8.67 \times 10^{12}$ | 4.5 |
| Epithermal | $3.92 \times 10^{11}$ | 5.0 |
| Fast | $1.89 \times 10^{12}$ | 0.01 |

Thus, 2.46 MBq per hour of Cu-64 was produced per 100 milligram of glass irradiated at the flux densities presented in Table 2. The radiation spectra from the samples were measured and are illustrated in FIG. 1. Table 3 presents the breakdown of isotopes present.

TABLE 3

| Radioisotope | Activity 24-hour | Activity 1 week |
|---|---|---|
| $^{64}$Cu | 1.65 mCi | 171 nCi |
| $^{24}$Na | 1.87 μCi | 7.0 nCi |
| $^{140}$La | 47.0 nCi | 2.6 nCi |
| $^{122}$Sb | 72.0 nCi | 12.1 nCi |
| $^{65}$Zn | <1 nCi | <1 nCi |
| $^{110}$Ag | 1.0 nCi | 1.0 nCi |
| $^{60}$Co | 1.7 mCi | 1.7 nCi |

To verify that copper does not leach out of the glass, one sample was mixed with 20 ml deionized water and a second sample was mixed with 20 ml saline. Both samples were incubated at 37 degrees Celsius for 2 days and then filtered. The filtered solutions were assayed in a dose calibrator and no activity was observed.

Example 2

A combination treatment/imaging microsphere glass composition may be prepared by dispersing oxides of natural copper and yttrium in an aluminosilicate glass matrix. Natural copper is about 69 percent Cu-63 and about 31 percent Cu-65. Yttrium is Y-89. Upon neutron irradiation, the Y-89 is activated to Y-90, the Cu-63 is activated to Cu-64 and the Cu-65 is activated to Cu-66. For imaging purposes, the activation of Cu-66 is irrelevant, since Cu-66 has a half-life if about 5.1 minutes and decays to negligible amounts within a few hours of the irradiation procedure. Cu-64 is a positron emitter and lends itself to PET imaging, having a low mean positron energy (resulting in less blurring) and a 'clean' energy spectrum (minimal non-PET gamma emissions). Moreover, Cu-64 emits a low energy beta particle (end-point energy of about 578 keV) about 39 percent of the time, which could contribute to the cancer treatment of the patient. Y-90 has a half-life of about 64 hours and emits beta particles with a mean energy of about 930 keV as well as energetic bremsstrahlung gamma rays. The 930 keV beta particles and gamma rays operate to kill tissue in close proximity (ideally cancerous tumor tissue) while sufficient quantities of the 511 keV gamma rays produced from annihilation of the positrons produced by decaying Cu-64 pass through the body and are detectible by PET imaging.

While the invention has been illustrated and described in detail in the drawings and foregoing description, the same is to be considered as illustrative and not restrictive in character. It is understood that the embodiments have been shown and described in the foregoing specification in satisfaction of the best mode and enablement requirements. It is understood that one of ordinary skill in the art could readily make a nigh-infinite number of insubstantial changes and modifications to the above-described embodiments and that it would be impractical to attempt to describe all such embodiment variations in the present specification. Accordingly, it is understood that all changes and modifications that come within the spirit of the invention are desired to be protected.

What is claimed is:

1. A substantially spherical body for imaging blood flow in a living organism, comprising:

a biologically stable glass matrix formed from materials that do not become significantly radioactive during neutron irradiation; and at least one non-radioactive isotope distributed substantially uniformly throughout the matrix and characterized by emission of a detectable amount of positron radiation and a maximum half-life of about four days upon neutron irradiation;

wherein the at least one non-radioactive isotope includes $^{63}$Cu and wherein the glass is a substantially boron-free aluminosilicate.

2. The substantially spherical body of claim 1 wherein the non-radioactive isotope is further characterized by a substantial lack of nuclear gamma emission upon neutron irradiation.

3. The substantially spherical body of claim 1 wherein the non-radioactive isotope is further characterized by an emission of positron radiation with a mean energy of below about 400 keV upon neutron irradiation.

4. The substantially spherical body of claim 1 wherein the non-radioactive isotope is further characterized by an emission of positron radiation with a mean energy of between about 250 keV and about 300 keV upon neutron irradiation.

5. The substantially spherical body of claim 1 wherein the biologically stable matrix has a maximum dimension of between about 5 micrometers and about 75 micrometers.

6. An injectable positron source for imaging blood flow in a living organism, comprising:

a plurality of substantially spherical biologically stable glass portions; and a predetermined amount of positron emitters distributed in each respective portion;

wherein the plurality of substantially spherical biologically stable portions emit sufficient positron radiation for PET imaging of an organ and wherein each respective substantially spherical biologically stable portion has a maximum dimension of between about 5 micrometers and about 75 micrometers; and wherein the positron emitters are $^{64}Cu$ atoms and wherein the glass is a substantially boron-free aluminosilicate.

7. The positron source of claim 6 wherein the glass includes between about 0.1 weight percent and 30 weight percent copper oxide.

8. The positron source of claim 6 wherein the positron emitters are introduced into the respective biologically stable portions as nonradioactive isotopes and wherein the nonradioactive isotopes are activated to become positron emitters through neutron irradiation.

9. The positron source of claim 6 wherein the respective biologically stable portions also include therapeutic nonradioactive isotopes; wherein the therapeutic nonradioactive isotopes are activated to become therapeutic radiation emitters through neutron irradiation; and wherein the therapeutic radiation is selected from the group including beta particles, gamma rays, and combinations thereof.

10. A substantially spherical body for administering therapeutic radiation and imaging blood flow in a living organism, comprising:

a biologically stable vitreous matrix formed from materials that do not become significantly radioactive during neutron irradiation;

a first non-radioactive Cu-63 isotope distributed substantially uniformly throughout the matrix and characterized by emission of a detectable amount of positron radiation and a maximum half-life of about four days upon neutron irradiation; and a second non-radioactive isotope distributed substantially uniformly throughout the matrix and characterized by emission of an effective amount of therapeutic radiation and a maximum half-life of about four days upon neutron irradiation;

wherein the therapeutic radiation is selected from the group including gamma radiation, beta radiation, and a combination of the beta and gamma radiation and wherein the biologically stable vitreous matrix is a substantially boron-free aluminosilicate glass.

11. The substantially spherical body of claim 10, wherein the second non-radioactive isotope is Y-89.

12. The substantially spherical body of claim 10, wherein the first non-radioactive isotope is distributed substantially uniformly throughout the matrix as a component of natural copper.

13. The substantially spherical body of claim 10, wherein the first non-radioactive isotope is distributed substantially uniformly throughout the matrix as an oxide.

* * * * *